(12) United States Patent
Patel

(10) Patent No.: US 10,940,008 B2
(45) Date of Patent: Mar. 9, 2021

(54) IMPLANT FOR BONE SEGMENT FUSION

(71) Applicant: ANJALI INVESTMENTS LLC, Lutherville-Timonium, MD (US)

(72) Inventor: Amit Patel, Lutherville-Timonium, MD (US)

(73) Assignee: ANJALI INVESTMENTS LLC, Lutherville-Timonium, MD (US)

( * ) Notice: Subject to any disclaimer, the term of this patent is extended or adjusted under 35 U.S.C. 154(b) by 0 days.

(21) Appl. No.: 17/071,686

(22) Filed: Oct. 15, 2020

(65) Prior Publication Data

US 2021/0022873 A1   Jan. 28, 2021

Related U.S. Application Data

(63) Continuation of application No. PCT/US2020/019194, filed on Feb. 21, 2020.
(Continued)

(51) Int. Cl.
*A61F 2/30* (2006.01)
*A61B 17/70* (2006.01)

(52) U.S. Cl.
CPC ...... *A61F 2/30771* (2013.01); *A61B 17/7032* (2013.01); *A61F 2/30988* (2013.01);
(Continued)

(58) Field of Classification Search
CPC .............. A61F 2/30988; A61F 2/30771; A61F 2002/30995; A61F 2002/30224; A61B 17/7032
See application file for complete search history.

(56) References Cited

U.S. PATENT DOCUMENTS 10,130,407 B2   11/2018  Castaneda et al.
2011/0257753 A1*  10/2011  Gordon ............... A61F 2/30756
                                            623/18.11
(Continued)

FOREIGN PATENT DOCUMENTS

WO    2017/123753 A1    7/2017

OTHER PUBLICATIONS

Written Opinion of the International Search Authority, PCT/US2020/019194, dated May 4, 2020.
(Continued)

*Primary Examiner* — Christian A Sevilla
(74) *Attorney, Agent, or Firm* — Andrew Berks; Ostrolenk Faber LLP

(57) ABSTRACT

A bone screw implant is provided for immobilizing the articular surfaces of two bone segments by securing, fusing, or compression the two segments. The implant may be fabricated from a porous biocompatible metal and have a cylindrical shape and fully or partially threaded and may have variable pitch threads and a variable diameter of the shaft. The implant may include a blunt tip or a fluted self-drilling tip and a headless screwdriver socket. Large pitch cancellous threads may be in the leading-end portion of the cylinder shaft, and smaller pitch cortical threads may be at the trailing edge portion of the shaft. The implant may be fenestrated, it may have a roughened surface, and it may be coated with an osteoconductive material. The implant may be cannulated. In a specific embodiment, the implant is used for immobilizing the articular surfaces of a sacroiliac joint.

17 Claims, 7 Drawing Sheets

Related U.S. Application Data

(60) Provisional application No. 62/837,290, filed on Apr. 23, 2019, provisional application No. 62/808,454, filed on Feb. 21, 2019.

(52) U.S. Cl.
CPC .............. *A61F 2002/3085* (2013.01); *A61F 2002/30224* (2013.01); *A61F 2002/30622* (2013.01); *A61F 2002/30863* (2013.01); *A61F 2002/30886* (2013.01); *A61F 2002/30995* (2013.01); *A61F 2310/00023* (2013.01); *A61F 2310/00131* (2013.01); *A61F 2310/00796* (2013.01)

(56) References Cited

U.S. PATENT DOCUMENTS

| | | | |
|---|---|---|---|
| 2012/0277804 A1* | 11/2012 | Bhatnagar | A61B 17/864 606/298 |
| 2015/0157376 A1* | 6/2015 | Martineau | B22F 5/06 419/2 |
| 2015/0209094 A1* | 7/2015 | Anderson | A61B 17/869 606/304 |
| 2016/0310188 A1* | 10/2016 | Marino | A61F 2/4601 |
| 2018/0042652 A1* | 2/2018 | Mari | A61B 17/8685 |
| 2018/0116814 A1* | 5/2018 | Sullivan | A61B 17/864 |
| 2018/0206897 A1 | 7/2018 | Palmer | |
| 2019/0167326 A1* | 6/2019 | Greenhalgh | A61B 17/864 |
| 2020/0353123 A1* | 11/2020 | Morris | A61L 27/12 |

OTHER PUBLICATIONS

Zimmer BioMet Tricor(TM) Brochure, copyright 2017.
Guoyuan Li et al., "In vitro and in vivo study of additive manufactured porous Ti6Al4V scaffolds for repairing bone defects," Scientific Reports, 2016, 6:34072, DOI: 10.1038/srep34072.

\* cited by examiner

IMPLANT FOR BONE SEGMENT FUSION

CROSS REFERENCE TO RELATED APPLICATIONS

This patent application claims priority under 35 U.S.C. § 120 to PCT International Patent Application No. PCT/US20/19194, filed Feb. 21, 2020, and to U.S. Patent Applications 62/808,454 filed Feb. 21, 2019, and 62/837,290 filed Apr. 23, 2019, the contents of which are incorporated by reference.

FIELD OF THE INVENTION

This invention pertains to screws for securing, fusing, and/or compressing the sacroiliac joint, vertebrae, and other bones, joints, or other bone segments.

BACKGROUND OF THE INVENTION

In orthopedics, there is frequently a need to stabilize bone segments as a result of fractures, joint dislocation, degenerative disease, or other causes. One approach to treating any of these conditions is the use of screws for securing, fusing, and/or compressing two bone segments together.

One method of treating a fracture across two bone fragments is driving a compression screw across the fracture site. Some compression screws may have a variable thread pitch along the length of the screw to aid in compressing the fracture. For fractures distal from the surface of the bone, it may be desirable to have a compression screw with no head, such that the screw can be inserted deeply into the bone. One example of such a fracture is sacroiliac joint dysfunction, but many other fractures are treated with screws to stabilize, compress and fuse bone segments.

Low back pain is a ubiquitous complaint and is second only to the common cold for medical office visits in the US. A common etiology of low back pain is sacroiliac (SI) joint dysfunction, also referred to as "sacroiliac joint instability" or "sacroiliac joint insufficiency" due to the lack of support of ligaments that normally stabilize the SI joint. Common symptoms include lower back pain, buttocks pain, sciatic leg pain, groin pain, hip pain, urinary frequency, and transient paresthesia. Pain can range from dull aching to sharp and stabbing and increases with physical activity. Symptoms also worsen with prolonged or sustained positions (i.e., sitting, standing, lying). The prevalence of SI related pain is estimated to be in about a quarter of all patients complaining of low back symptoms.

The SI joint is a complex, irregular synarthrodial joint with extensive soft tissue and ligamentous support and innervation. The joint serves as a transition from the axial spine to the pelvis. The joint has a ventral portion with articular cartilage and synovial fluid and dorsal and ventral portions having a ligamentous structure. The total motion of the joint is typically between 1°-2° rotation (nutation/counter-nutation) and 5 mm translation between sitting or standing.

Dysfunction of the SI joint in part is thought to be related to pathological motion as the normal joint allows for only minimal nutation and counter-nutation and/or degeneration of the joint from various etiologies such as trauma, repetitive injuries, childbirth, infection, and adjacent level disease (i.e., fusion of the L5-S1 segment).

Common symptoms of SI pain include pain at the sacral sulcus, sciatica-like symptoms, difficulty bearing weight to the affected side, and difficulties with static activities.

Fusion of SI joint was introduced in 1921. Smith-Petersen, M. N. (1921) "Arthrodesis of the Sacroiliac Joint. A New Method of Approach." *Journal of Bone and Joint Surgery*, 67, 157-159. At the time diagnosis was made clinically, the surgical options were limited to rather large, open procedures. The older literature suggested more than adequate rates of success with such procedures. In the 1980s instrumented fixation became common. Subsequent authors, however, were unable to reproduce similar clinical results.

Given the extensive nature and dissection of the proposed surgical solutions, the procedures themselves were wrought with complications that included persistent pain and deep wound infections. Throughout the mid-$20^{th}$ century and into even the 1990s, enthusiasm waned for open surgical solutions for the SI joint. Even the diagnosis itself was largely abandoned.

Common non-surgical treatment options include therapy, support braces, medications, and guided injections. If non-surgical treatments fail to provide adequate or sustainable relief, a minimally invasive surgery (MIS) option can be considered with the goal of stabilizing and/or fusing the SI joint.

Throughout the early 1990s and into the $21^{st}$ century, although substantial advancements were not made in the diagnosing of SI pain, minimally invasive surgical options with improved clinical outcomes and with less morbidity than open procedures resulted in a reemergence of the diagnosis and investigational studies to better understand the disease. This in turn, ushered in a plethora of implants designed to stabilize the SI joint in using minimally invasive techniques.

To eliminate motion across the SI joint there must be a successful fusion between the sacrum and ilium bones that comprise the SI joint. The fusion of any two bone structures is facilitated by stability. Stability is understood as the reduction of motion across the surfaces and is enhanced by compression which creates frictional contact between the surfaces.

Others have disclosed methods for the improvement of stability and structural integrity across the joint through osseous ingrowth through apertures/fenestrations on the body of the implant.

U.S. Pat. No. 6,053,916 discloses an implant with apertures on the body of the implant to allow for osseous ingrowth but does not disclose an implant having a porous structure and osteoconductive material coating for further bone growth enchantment.

US 2016/0310188 A also discloses a SI joint implant with fenestrations on the body of the implant.

Many patented implants are threaded. However, none have the combination of being porous, fenestrated, surface treated, and coated with osteoconductive materials to enhance further bone growth.

SUMMARY OF THE INVENTION

In order to address the above mentioned concerns, this invention provides a threaded implant for the stabilization, fusion or compression of the sacroiliac joint or other bone joints or bone segments, including compression and fusion of fractures. In an embodiment, the implant is fabricated from a compatible titanium or tantalum metal or alloy thereof. In an embodiment, the implant is porous, fenestrated, surface treated, and coated with osteoconductive materials to enhance further bone growth. In an embodiment, an internal set of threads can support a feature such a pedicle screw, extractor, inserter, or a base for an end cap.

Various thread embodiments are provided. In one embodiment, the implant is fully threaded with large pitch cancellous threads in the distal section, and smaller pitch cortical threads in the proximal section. In another embodiment, a central section of the implant has no threads. In another embodiment, the implant may have uniform threads the entire length, which can be large pitch cancellous threads or smaller pitch cortical threads.

Accordingly, in an embodiment, an implant for bone fusion or fixation is provided. In an embodiment, the implant is a cylindrical threaded implant fabricated from a titanium or tantalum metal or alloy with a similar modulus of elasticity to the bone, wherein the titanium or tantalum metal or alloy is a porous material with pore sizes ranging in 100 to 900 µm and a porosity of 60-65%. In an embodiment, the shaft (120) of the cylinder of the implant has a diameter between 4 mm to 14 mm and length between 10 mm to 280 mm. The implant has a distal section (122) with a distal end (125), and a headless proximal section (123) and a proximal end (150) having a socket (152) for attachment to a tool that can rotate to screw the implant into place. The implant is threaded with large pitch cancellous helical threads (142) on a portion of the shaft (120), or and smaller pitch cortical helical threads (144) on a proximal portion of shaft (123), or both. In an embodiment, the implant is surface treated to have a roughened surface and is coated with hydroxyapatite (HA) or tri-calcium phosphate (TCP) or both.

In an embodiment, the implant has large pitch cancellous helical threads (142) on the shaft on a portion of the distal section, and smaller pitch cortical helical threads (144) on the shaft on a portion of the proximal section.

In an embodiment, the implant has a channel (134) through the center with openings at the distal end (130) and proximal end (132) for accepting a guidewire.

In an embodiment, the implant has one or more fenestrations (160). In an embodiment, the implant has internal threads (170) for the attachment of an additional device such as an inserter, extractor, end cap, or modular tulip (as seen in standard pedicle screws).

In an embodiment, the distal end may be a self-drilling tip (126) with one or more teeth (127), or the distal end may be a blunt tip (129).

In an embodiment, the shaft of the implant in the section with cancellous threads may have a smaller maximum diameter than the maximal diameter of the shaft in the section with the cortical threads, and wherein the maximum diameter of the cancellous threads are slightly smaller than the maximum diameter of the cortical threads.

In an embodiment, threads are provided along the entire length of the implant. In an embodiment, a central section along the longitudinal axis of the implant has no threads on the shaft. In an embodiment, the implant has a hollow core.

In an embodiment, the fenestrations are perforations through the shaft of the implant that may be elongated on the longitudinal axis. The fenestrations may include a channel that penetrates the implant body in a latitudinal direction. The threads may be interrupted over the fenestrations, or the threads may be continuous over the fenestrations.

In an embodiment, the implant may have uniform cortical helical threads on the entire length of the shaft. In an embodiment, an implant may have uniform cortical helical threads on the entire length of the shaft and have a uniform shaft diameter.

In an embodiment, the implant is used to immobilize, fuse, or compress the articular surfaces of any bone segments or fragments, including the sacroiliac joint, the tibiotalar joint of the ankle, midfoot bones, and wrist bones.

In embodiment, a sacroiliac joint fusion implant for immobilizing the articular surfaces of sacroiliac joint is provided with a cylindrical threaded implant fabricated from a titanium or tantalum metal or alloy with a similar modulus of elasticity to bone, wherein the titanium or tantalum metal or alloy is a porous material with pore sizes ranging in 100 to 900 µm and a porosity of 60-65%. The one or more helical thread regions between the ends may have larger pitch threads proximal to the blunt nose end of the implant and smaller pitch threads towards the back end. The implant may have a central cannulated channel extending between the two ends. The implant may include screwdriver socket at the back end. The implant may be fabricated from porous titanium or tantalum or an alloy thereof, with a porosity between 60-65% with pore sizes between 100 to 900 um, and the implant may have a roughened surface that is fully coated with hydroxyapatite (HA) or tri-calcium phosphate (TCP) coating.

In an embodiment, a method for fusion or immobilization of the articular surfaces of the sacroiliac joint in relation to one another includes the steps of placing the implant as described herein on a guidewire, drilling a suitable borehole transverse to the sacroiliac joint, and implanting the implants transversely across the articular surfaces and through the sacrum and the ilium bones.

In an embodiment, a method for fusion or immobilization of the articular surfaces of the sacroiliac joint in relation to one another includes the steps of placing the implant as described herein on a guidewire, drilling a suitable borehole in-line to the sacroiliac joint, implanting the implants in-line with the articular surfaces of the sacroiliac joint.

DESCRIPTION OF THE DRAWINGS

FIG. 17a shows a guide wire implanted. FIG. 17b shows the guidewire and a drill bit creating a borehole. FIGS. 17c and 17d show an implant being inserted. FIG. 17e shows a lateral view of an implant in place. FIG. 17f is a coronal view of an installed implant. FIG. 17g is a posterior view of an installed implant.

FIG. 18A shows a posterior view. FIG. 18B shows a lateral view, with the posterior on the right. FIG. 18C shows a partial posterior view, with the bone structures rotated slightly counterclockwise.

DETAILED DESCRIPTION

This invention provides a cylindrical, threaded, porous, coated implant for the fusion, stabilization, or compression of two bone segments. One example is fusion and stabilization of the sacroiliac (SI) joint. In an embodiment, the implant is used for arthrodesis of two bone segments in need of fusion. The implant is fabricated from a biocompatible metal and has the unique combination of features including a fluted or blunt tip, variable or uniform thread pitches, use of a porous material, roughened surface, and a coating with an osteoconductive material. The blunt tip is intended to minimize the risk of injury during implantation and to surrounding soft tissue structures; however, a sharper tip could also be fashioned that would allow for a self-tapping and/or self-drilling capability. The inventive implants are implanted by drilling a bore hole slightly smaller than the largest diameter of the implant and screwing the implant into position with a screwdriver.

In an embodiment, the implant is made of titanium or tantalum to match the modulus of elasticity of bone and is fully porous with pore sizes ranging in 100 to 900 um (micron) to facilitate in-growth and have a porosity of 60-65% to mimic cancellous bone, which would allow for better osseointegration. In addition, the implant would be either a solid porous implant and/or slotted/fenestrated to allow for graft placement.

In an embodiment the implant has a diameter of 4 mm to 14 mm and length from 10 mm to 280 mm. In use, a kit may be provided for use in the operating theater with a variety of sizes.

In an embodiment, all surfaces of the implant are roughened with a macro surface roughness which may be accomplished with a technique such as grit blasting, acid etching, or plasma spray coating (also called thermal spray coating).

In an embodiment, all surfaces of the implant are coated with hydroxyapatite (HA) and/or tricalcium phosphate (TCP), with a coating thickness of approximately 35 μm (range 15-50 μm). Both HA and TCP are osteoconductive materials that encourage bone growth.

In an embodiment of the present invention, the implant is cannulated to allow for insertion via a guidewire.

Figure 8:
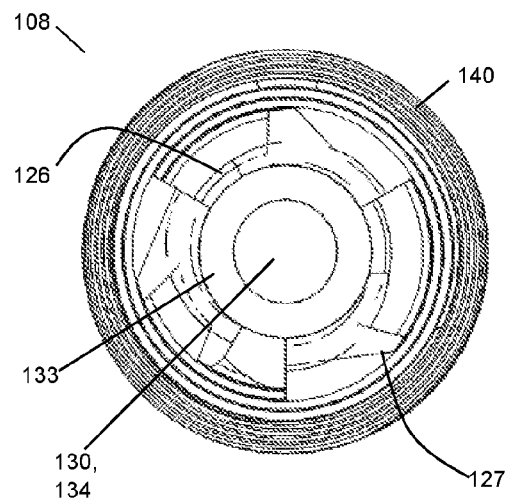
FIG. 8 is an elevation view of the distal end of the implant of FIG. 4
Figure 9:
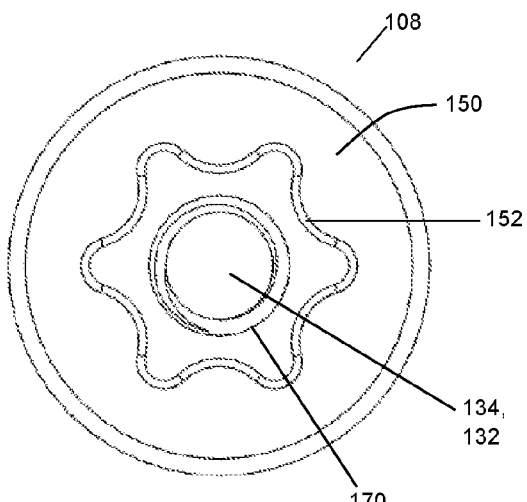
FIG. 9 is an elevation view of the proximal end of the implant of FIG. 4
Figure 10:
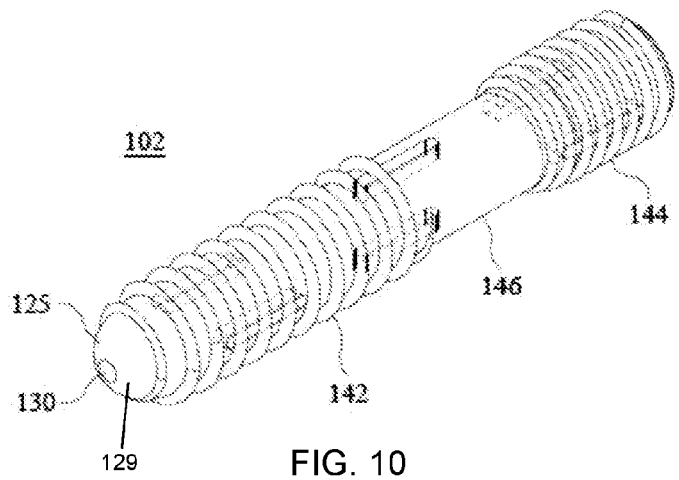
FIG. 10 is a perspective view of an alternative embodiment, similar to FIGS. 1-3, but having a waist section with no threads.
Figure 11:
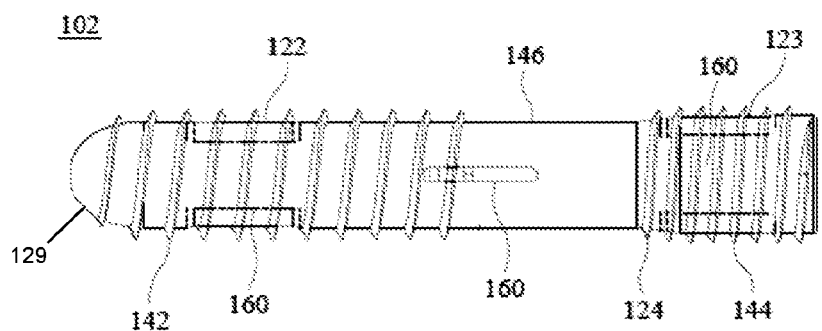
FIG. 11 is an elevation view of the embodiment of FIG. 4.

The implant is either fully threaded as shown on FIGS. 1-9 and 12-13 to stabilize the joint, or partially threaded as shown on FIGS. 10-11 to stabilize and compress the joint. The threads may vary in size and pitch. In an embodiment, the implant may have larger pitch cancellous threads in a distal section, and small pitch cortical threads in a proximal section. This configuration will compress two bone fragments, drawing them together for arthrodesis of the interface between two bone segments. In an embodiment when used for compression of the SI joint, the portion of the implant inserted into the sacrum may have large pitch cancellous threads, while the portion of the screw that secures to the ilium would have smaller pitch cortical threads. In an embodiment, the implant may have uniform threads (FIGS. 12-13), which stabilizes the joint.

Figure 1:
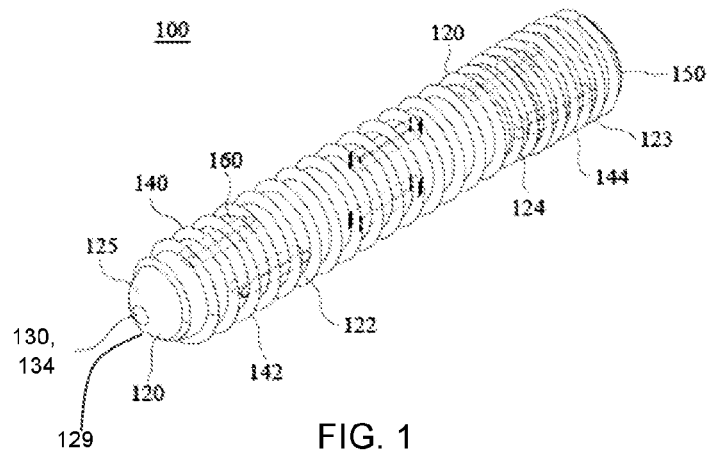
FIG. 1 is a perspective view showing the front (or distal end) of an embodiment of the inventive implant, showing a blunt forward end, larger pitch threads at the front and smaller pitch threads towards the back. Also shown at the tip is an opening for the cannula channel.

FIG. 1 is a perspective view of an embodiment of the inventive implant 100, showing the body 120 of the implant, having a blunt nose 129 (the distal end), which is the leading end of the implant and a back end 150 (the proximal end).

As used herein, the "distal" and "proximal" descriptors are in relation to the surgeon implanting the device. Thus, the nose (or tip) end (125) is distal to the surgeon during implantation. This distal end is also referred to as a "tip," the "front," "nose," or "leading end." The back end 150 with the screwdriver socket (152) is closer to the surgeon and is therefore the proximal end. The inventive implants have a longitudinal axis running from the nose end 125 to the back end 150. This is illustrated as line A-A in FIG. 4. A latitudinal cross section can be made at any point perpendicular to the longitudinal axis.

Figure 2:
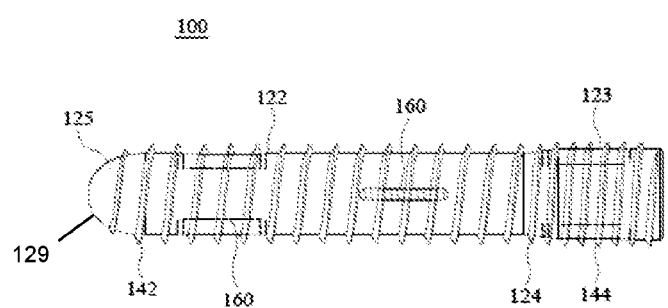
FIG. 2 is an elevation view of the implant of FIG. 1, showing about the front two-thirds having larger threads and smaller shaft diameter than the rear one-third, which has smaller threads and a slightly larger overall diameter.
Figure 3:
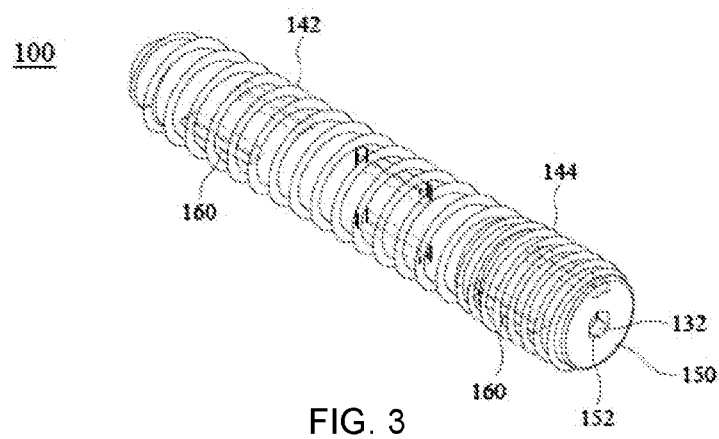
FIG. 3 is a perspective view showing the rear (or proximal end) of the implant of FIG. 1. The back end has an opening for the cannula channel and a socket for a screwdriver tip. A hex socket is shown, but other embodiments are possible.

As shown in FIGS. 1-3, implant embodiment 100 has a blunt tip 129 at the nose 125. Other embodiments of nose 125 possible, for example embodiment 108 as shown in FIGS. 4-9. The blunt tip nose 129 may be useful to minimize tissue damage during insertion of the implant.

In the embodiment 100 illustrated in FIGS. 1-3, the helical threads 140 on the distal end of the implant are large pitch cancellous threads 142. In an embodiment, these threads may have a pitch of 2.75 mm and a thread height H of 2.00 mm. As shown in FIGS. 1-3, the forward 75% (approximately) of the implant employs cancellous threads, and the proximal remainder of the implant has smaller pitch cortical threads.

In the embodiment illustrated in FIGS. 1-3, the threads 140 on the proximal end of the implant are smaller pitch cortical threads 144. As illustrated, the cortical threads have a pitch of 1.75 mm and a thread height H of 1.50 mm.

In the embodiment illustrated in FIGS. 1-3, the implant body 120 does not have a uniform diameter. This is a function of the requirement that the cortical threads have a slightly larger overall diameter (Dmaj) than the cancellous threads. This is necessary because during implantation, the cortical threads follow the cancellous threads into the bore hole drilled for the implant. If the rear thread were not slightly larger, the implant would not nest snugly in its final position. Since the cancellous threads in the forward two-thirds of the illustrated implant are larger threads, the body of the implant must be reduced in diameter to accommodate the larger threads in the cancellous-threaded section, and the requisite smaller Dmaj than the cortical-threaded section. A transition zone 124 is present between the two sections.

Thus, a representative set of dimensions for the two zones of the implant (FIGS. 1-3 and 10-11) may be:
  Cancellous threads, Dmaj=10.5 mm, Dmin=8.5 mm, P=2.75 mm
  Cortical threads, Dmaj=11.0 mm, Dmin=9.5 mm, P=1.75 mm Where Dmaj is the major diameter, which is the maximum diameter of the thread. Dmin is the minor diameter, which in effect is the diameter of the body of the shaft in this embodiment. P is the thread pitch. Typical ISO 261 or Unified Thread Standard (UTS) dimensions may be used for the screw thread dimensions.

In the embodiment of FIGS. 4-7, the proximal section with cortical threads has an increased diameter with a horn-shaped profile with a maximal diameter at the proximal end 150.

Thus, as illustrated in FIGS. 1-3, the maximal diameter (Dmaj)(cancellous) of the cancellous threads is 0.5 mm smaller than the maximal diameter (Dmaj)(cortical) of the cortical threads. In an embodiment, this diameter differential may vary from about 0.1 mm to 1.0 mm.

The embodiment shown in FIGS. 1-3 illustrates a typical embodiment of this invention. The implant 100 comprises a cylindrical body, circular in latitudinal cross section, that is about 10-280 mm long. The length of the implant in these illustrations is 60 mm. A blunt tip 125 is shown on the distal end for minimizing damage to tissues during the insertion procedure. A cannula channel 134 may be provided along the longitudinal axis of the implant, for placement using a guide wire. The distal opening of the cannula channel is 130. The forward (distal) approximately 75% of the length of the implant, 122, is threaded with cancellous threads 142. The proximal section of the shaft, 123, is threaded with cortical threads. As discussed above, the cancellous section 122 has a smaller diameter than cortical section 123.

FIG. 3 is a perspective view showing the distal (back) end 150 of the implant 100 of FIG. 1. The structure of the back end is typical for all implants of this invention. The proximal end of the implant is headless and includes a screwdriver socket 152, depicted in FIG. 3 as a hex socket. This socket can be in any of several shapes for accepting a screwdriver, for example, a Phillips screw socket, "Torx" socket, or a hex socket. Also depicted in FIG. 3 is orifice 132, which is the proximal outlet for the cannula channel along the centerline of the implant. The overall structure of the proximal end of the inventive implants (150, 152, 132) may the same across other embodiments, for example those depicted in FIGS. 4, 10, and 12.

Figure 4:
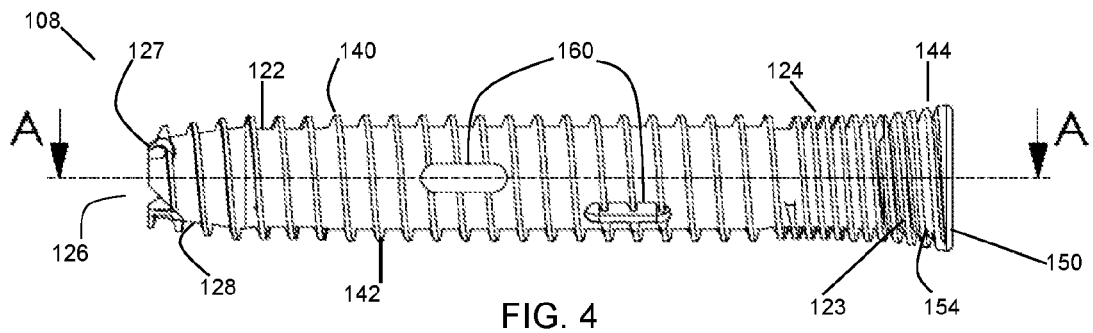
FIG. 4 is an elevation view of an alternative embodiment of the inventive implant.
Figure 5:
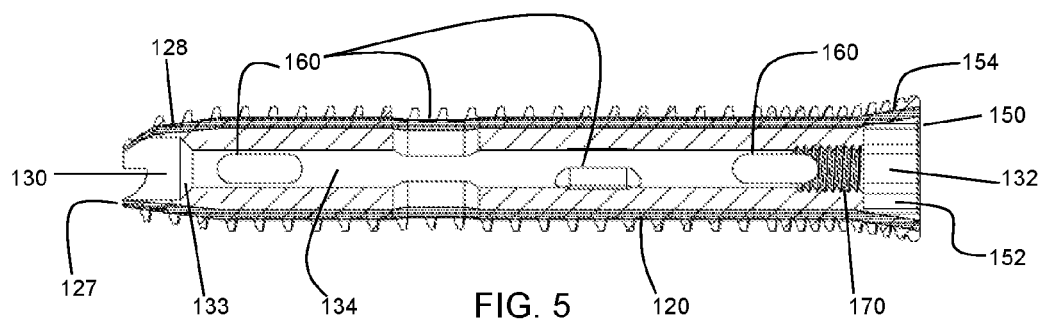
FIG. 5 is a cross section of the embodiment shown in FIG. 4, cut through the line marked A-A.
Figure 6:
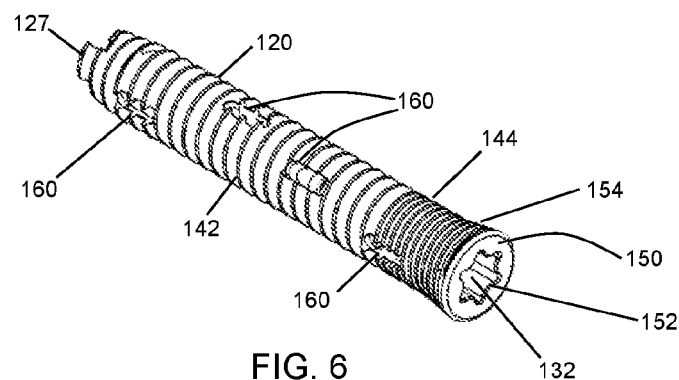
FIG. 6 is a perspective view of the proximal end the embodiment of FIG. 4.
Figure 7:
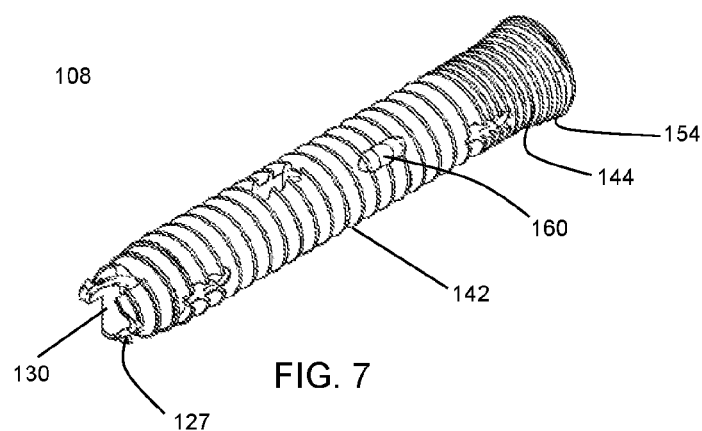
FIG. 7 is a perspective view of the distal end of the embodiment of FIG. 4.

An alternative embodiment of a fully threaded implant 108 is shown in FIGS. 4-9. This embodiment includes a taper 128 in shaft 120 towards tip 126. Tip 126 is fluted and has teeth 127. This fluted tip can also be termed a "self-tapping" or "self-drilling" screw tip. FIG. 4 is an elevation view of this implant. Several fenestrations 160 are shown, for bone through growth. The fenestrations are shown as elliptical perforations that pass completely through the body 120 of the implant. The proximal end of implant 108 is has cortical threads and is flared (154) outward slightly, with a horn-like shape. A perspective view of the proximal end of 108 is shown in FIG. 6. A perspective view showing the distal end is in FIG. 7.

A cross sectional view of implant 108 is shown in FIG. 5, showing a view through line A-A is FIG. 4. Body 120 is seen with taper 128 at the distal end and flare 154 at the proximal end. Central channel 134 is shown, along with channel taper sections 133. The cross section bisects one of fenestrations 160.

FIG. 5 also shows internal threads 170. These threads are a potential feature of any embodiment of this invention. Threads 170 are female threads in central channel 134 at the proximal end of the implant, adjacent to the screwdriver socket 152. These threads can be used for a variety of purposes. For example, a short shaft screw (i.e., having male threads) with a tulip as seen with standard pedicle screws can be inserted for anchoring a rod system. Other examples that can be screwed into threads 170 include an inserter, an extractor, or a plug or cap that may extend to cover end 150. The cap can be used to minimize loss of bone grafts. For example, channel 130 may be packed with bone fragments from an autograft or allograft, which may facilitate bone growth. A cap over 150 will keep the bone fragments in place.

End views of the implant 108 are shown in FIGS. 8 and 9. FIG. 8 is an elevation view of the distal tip, showing flutes (teeth) 127, central channel 134, taper 133, and threads 140. FIG. 9 is an elevation view of the proximal end (150) of the implant, shown screwdriver socket 152 (a torx socket is shown), channel 134 and opening 132, and threads 170.

The embodiment 102 in FIGS. 10-11 is similar to FIGS. 1-3, except that this embodiment has a waist section 146 with no threads. Thus, there is a section of cancellous threads 142 on a distal portion of the body, and a section of cortical threads 144 on the proximal section of the body, and no threads in the center section. This type of implant may be used for compression of joints, including the SI joint.

Figure 12:
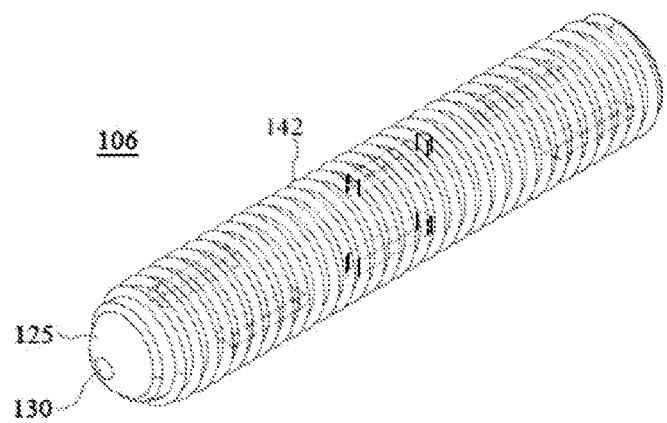
FIG. 12 is a perspective of an alternative embodiment of the inventive implant, having uniform cortical threads along the entire shaft.
Figure 13:
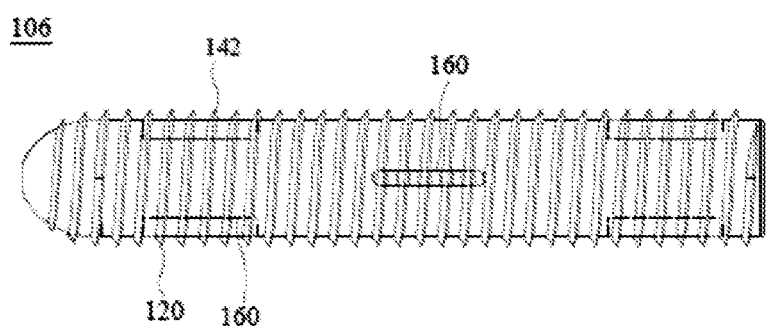
FIG. 13 is an elevation view of the embodiment of FIG. 12.

The embodiment 106 of FIGS. 12-13 has uniform thread dimensions and a uniform shaft diameter. In this embodiment as shown, the implant has cortical thread dimensions (144) throughout, but an alternative embodiment can have larger diameter cancellous threads throughout. FIGS. 10-13 are illustrated with blunt tip 125/129, but these embodiments are also possible with fluted tip 126/127.

In an embodiment, the implants 100, 102, 106, and 108 may have perforations 160 for bone through-growth (also termed herein "fenestrations"). In an embodiment, the threads 140, 142, or 144 are interrupted over the fenestrations. In an alternative embodiment, the threads are continuous over the fenestrations. In an embodiment, the fenestrations 160 penetrate completely through the body of the implant latitudinally. In an embodiment, the fenestrations are slots or apertures, elongated in the longitudinal direction of the implant.

In a further embodiment, the implant may have a hollow core. In an embodiment, the implant may have a solid core, that is, without a central channel 134.

In an embodiment, the entire implant is fabricated from medically compatible tantalum, titanium, tantalum alloy, or titanium alloy. For example, an appropriate titanium alloy may be titanium 6Al4V and 6Al4V ELI (ASTM Standard F1472, https://www.astm.org/Standards/F1472.htm (see also https://en.wikipedia.org/wiki/Ti-6Al-4V)), which are alloys made with about 6% aluminum and 4% vanadium. An appropriate tantalum alloy may be tantalum alloyed with 2.5% to 10% tungsten, or 40% niobium. These materials are known to have good biocompatibility and match the modulus of elasticity of bone. In an embodiment, the implant may be manufactured from a titanium alloy in accordance with ASTM F136, or where exterior surfaces are coated with medical-grade commercially pure titanium (CP Ti) per ASTM F1580.

In an embodiment, the implant may be fabricated from a titanium or tantalum material as described above that is also porous, which is known to enhance bone in-growth, for example with pore sizes ranging in 100 to 900 μm and with a porosity of 60-65% to mimic cancellous bone. Porosity is a measure of the void (i.e. "empty") spaces in a material and is a fraction of the volume of voids expressed as a percentage. Pore sizes of about 600 μm have been recommended as optimal for bone ingrowth (N. Taniguchi, et al., "Effect of pore size on bone ingrowth into porous titanium implants fabricated by additive manufacturing: An in vivo experiment," *Mater Sci Eng C Mater Biol Appl.* 2016 February; 59:690-701. doi: 10.1016/j.msec.2015.10.069. Epub 2015 Oct. 28). In an embodiment, the pore sizes may be 300-400 µm. Li, G., Wang, L., Pan, W. et al. In vitro and in vivo study of additive manufactured porous Ti6AI4V scaffolds for repairing bone defects. Sci Rep 6, 34072 (2016). https://doi.org/10.1038/srep34072. In an embodiment, any pore size recitation herein may have a tolerance of ±50 µm. In an embodiment, the pores may have uniform shapes, or have random shapes.

The combination of fenestrations, surface roughness, HA or TCP coating, and porosity will facilitate bone in-growth which is desirable for fusion of the implants to surrounding bone.

In use, the implants are preferably implanted using minimally invasive methods. In an exemplary method, there are four principal steps of the surgical procedure. These are: minimally invasive lateral access via dilators and image guidance, joint preparation via drills or currettes, bone graft placement, and implant delivery. Various implant trajectories are possible.

Figure 14:
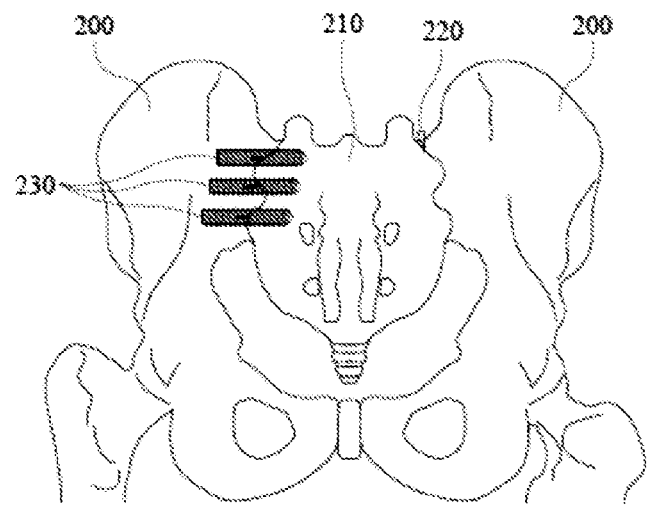
FIG. 14 is a posterior view of the pelvic bone structure, showing typical implant trajectories that secure and stabilize the sacroiliac joint.

In one aspect, a method is provided for stabilizing the SI joint by inserting a single or multiple implants from a lateral to medial direction, transverse to the SI joint. FIG. 14 is a posterior view of the pelvic bone structure, showing transverse implant placements 230 that secure and stabilize the sacroiliac joint 220 with the distal portion of the implant inserted in the sacrum 210 and the proximal portion of the implant embedded in the ilium 200.

Figure 15:
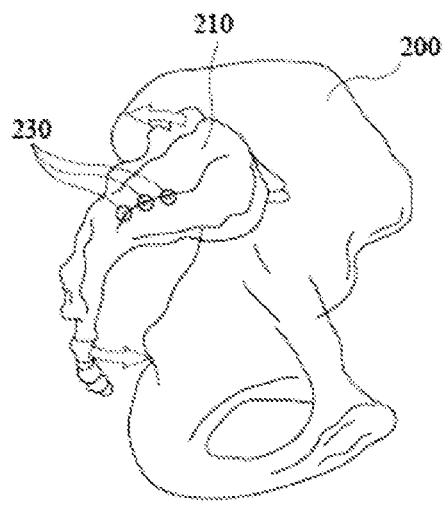
FIG. 15 is a sagittal view of the pelvic bone structure showing implant trajectories.

FIG. 15 is a sagittal view of the pelvic bone structure showing implant trajectories and the movement of the sacrum 210 with respect to ilium 200 is shown with arrows, with the implants 230 traversing the sacrum 210 and ilium 220. The method includes dissecting through the gluteal muscles, drilling/advancing the implant through the ilium, traversing the SI joint, entering the sacrum and stopping just lateral to the sacral foramen and/or neural elements.

Figure 16:
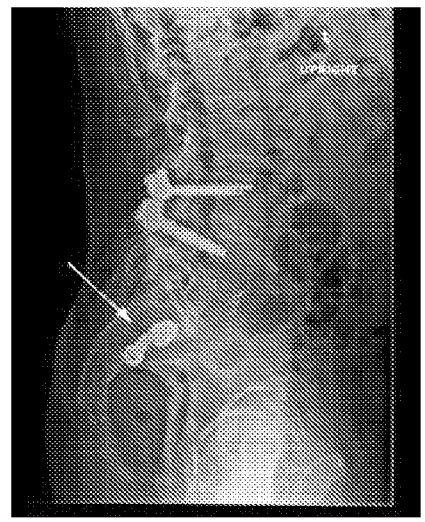
FIG. 16 is an x-ray radiograph showing implants, sagittal view.

FIG. 16 is an x-ray radiograph sagittal view showing various implants, including sacroiliac joint implants designated by an arrow in the transverse trajectory.

Figure 17:
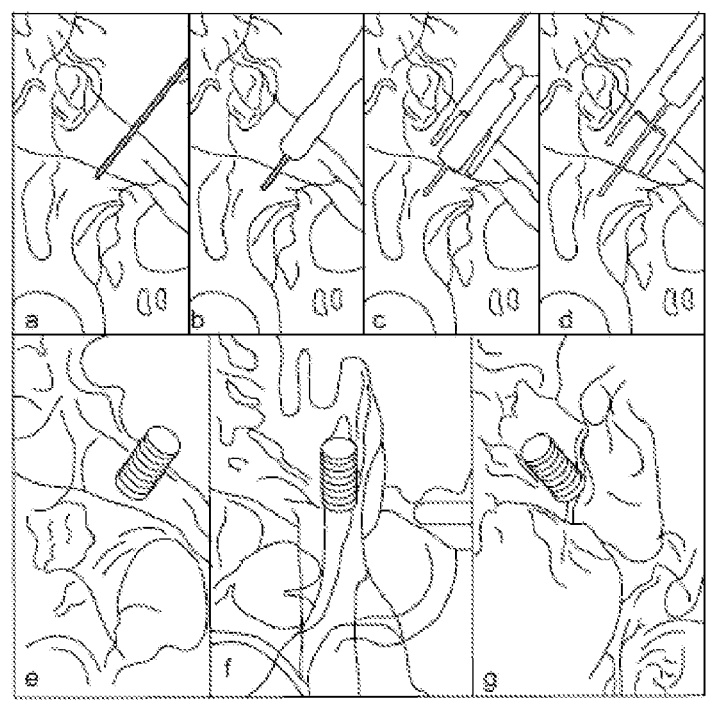
FIGS. 17a-g show the implant being placed in a distraction-interference method.
Figure 18:
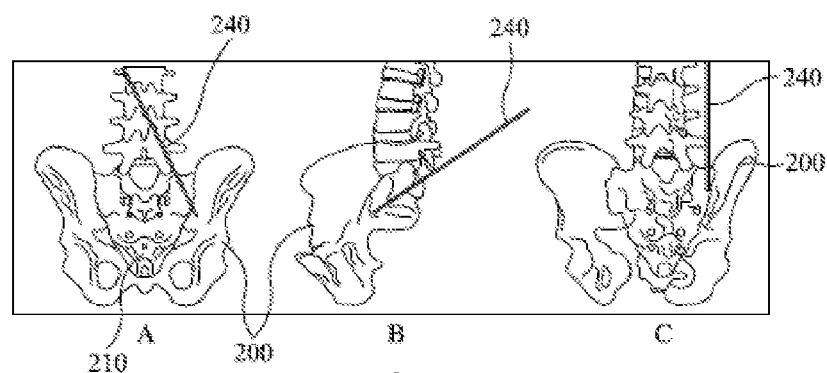
FIGS. 18A-C show various views of trajectories that may be used for the inventive implants for stabilization, fusion, or compression of the sacroiliac joint.

In another embodiment, the method for stabilizing the SI includes inserting the implant through an in-line trajectory, namely in a distraction arthrodesis manner in which the implant would enter at the posterior/superior aspect of the joint and advance caudally and in-line with the SI joint, as shown on FIGS. 17 and 18.

FIG. 17 is a series of x-ray radiographs for a similar implant, showing the implant being placed using a distraction-interference method. FIG. 17a shows a guide wire implanted. FIG. 17b shows the guidewire and a drill bit creating a bore hole along the guide wire. FIGS. 17c and 17d show the implant being inserted. FIG. 17e shows a lateral view of an implant in place. FIG. 17f is a coronal view of the installed implant. FIG. 17g is a posterior view of the installed implant.

FIG. 18 shows various views of a trajectory 240 that may be used for this implant, in a trajectory where the implant is positioned within the sacroiliac joint, rather than across the joint. FIGS. 12A-C show different views of the same trajectory 240 that is made from the posterior to the anterior direction at an angle pointing downward, i.e., the caudal direction. FIG. 18A shows a posterior view with the implant inserted into the joint across the center plane of the patient. FIG. 18B shows a lateral view of the same trajectory, with the posterior on the right. FIG. 18C shows a partial posterior view, with the bone structures rotated slightly counterclockwise.

In an exemplary procedure, a 1.5-2 cm incision is made, and a dilator and guide pin are used to access the ilium and SI joint under fluoroscopic guidance. A cannulated drill is then advanced over the guide pin to create an osseous tunnel through the ilium and/or sacrum. The drillings are collected for use in the bone graft, avoiding the need for direct ICBG harvest. The joint is prepared by removing cartilage and decorticating the joint area surrounding the tunnel, while irrigation and suction are used to extract joint tissue. Approximately 5 cc bone graft, including autologous bone from the drillings, is then packed into the implant.

Fixation is then achieved with at least one cannulated implant, and one or more additional implants to ensure rotational stability. Final fluoroscopic images are obtained to confirm correct placement, and the deep tissues and skin incision may be infiltrated with bupivacaine and epinephrine for postoperative pain control. Fusion status is typically assessed with CT 12 months after the procedure if indicated.

| Drawings | Legend |
|---|---|
| 100 | Implant with continuous threads cancellous and cortical |
| 102 | Implant with no threads in the center section |
| 106 | Implant with cortical threads only, uniform shaft diameter |
| 108 | Implant with fluted tip, flared proximal section |
| 120 | Implant body (shaft) |
| 122 | Implant body (shaft) - cancellous (distal) section |
| 123 | Implant body (shaft) - cortical (proximal) section |
| 124 | Body transition section |
| 125 | Nose (tip) (distal end) of implant |
| 126 | Self-drilling tip |
| 127 | Teeth (flutes) on distal tip |
| 128 | Taper on shaft at distal end |
| 129 | Blunt tip |
| 130 | Central channel opening at the distal end |
| 132 | Central channel opening at the proximal end |
| 133 | Internal taper in central channel |
| 134 | Central channel |
| 140 | Threads |
| 142 | Cancellous Threads at the distal end |
| 144 | Cortical Threads at the proximal end. |
| 146 | Central section with no threads |
| 150 | Back (proximal) end |
| 152 | Screwdriver socket |
| 154 | Flare in proximal section |
| 160 | Perforation for bone in-growth |
| 170 | Internal threads |
| 200 | Ilium |
| 210 | Sacrum |
| 220 | Sacroiliac joint |
| 230 | Inventive implants in position |
| 240 | Implant trajectory |

The invention claimed is:
1. An implant for bone fusion or fixation, comprising
  a. A cylindrical threaded implant fabricated from a titanium or tantalum metal or alloy with a similar modulus of elasticity to the bone, wherein the titanium or tantalum metal or alloy is a porous material with pore sizes ranging in 100 to 900 µm and a porosity of 60-65%;
  b. wherein the cylinder comprises a shaft (120), wherein the shaft has a diameter between 4 mm to 14 mm and length between 10 mm to 280 mm;
  c. wherein the implant has a distal section (122) with a distal end (125);
  d. wherein the implant has a headless proximal section (123) and a proximal end (150) having a socket (152) for attachment to a tool that can rotate to screw the implant into place;

e. wherein the implant is threaded with large pitch cancellous helical threads (142) on a portion of the shaft (120), or smaller pitch cortical helical threads (144) on a portion of shaft (123), or wherein the implant has uniform threads (FIG. 12, 142);
f. wherein the implant has at least one fenestration (160) penetrating through the body of the implant latitudinally, where the fenestration facilitates bone through-growth;
g. wherein the implant has a roughened surface; and
h. wherein the implant with the roughened surface is coated with hydroxyapatite (HA) or tri-calcium phosphate (TCP) or both.

2. The implant according to claim 1, further comprising threads along the entire length of the implant.

3. The implant according to claim 1, further comprising a central section having no threads on the shaft.

4. The implant according to claim 1, wherein the implant has large pitch cancellous helical threads (142) on the shaft on a portion of the distal section, and smaller pitch cortical helical threads (144) on the shaft on a portion of the proximal section.

5. The implant according to claim 1, wherein the distal section has large pitch cancellous threads, the proximal section has smaller pitch cortical threads, and the proximal section has a flare (154).

6. The implant according to claim 1, wherein the shaft in the section with cancellous threads (122) has a smaller diameter than the diameter of the shaft in the section with the cortical threads (123), and wherein the maximum diameter of the cancellous threads are slightly smaller than the maximum diameter of the cortical threads.

7. The implant according to claim 1, wherein the implant has a channel (134) through the longitudinal axis with openings at the distal end (130) and proximal end (132) for accepting a guidewire.

8. The implant according to claim 1, wherein the porous titanium or tantalum metal or alloy has pore sizes of 300 to 400 μm.

9. The implant according to claim 1, wherein the porous titanium or tantalum metal or alloy has a pore size of 600 μm.

10. The implant according to claim 1, wherein the implant has internal threads (170) for the attachment of an additional device.

11. The implant according to claim 1, wherein the distal end comprises a self-drilling tip (126) with one or more teeth (127).

12. The implant according to claim 1, wherein the distal end comprises a blunt tip (129).

13. The implant according to claim 1, wherein the implant is used to immobilize the articular surfaces of a sacroiliac joint.

14. A fusion or fixation implant for immobilizing the articular surfaces of a joint or segment of bone or fracture comprising:
a. A cylindrical threaded implant fabricated from a titanium or tantalum metal or alloy with a similar modulus of elasticity to the bone, wherein the titanium or tantalum metal or alloy is a porous material with pore sizes ranging in 100 to 900 μm and a porosity of 60-65%;
b. wherein the cylinder comprises a shaft (120), wherein the shaft has a diameter between 4 mm to 14 mm and length between 10 mm to 280 mm;
c. wherein the implant has a distal section with a fluted distal end (126, 127);
d. wherein the implant has a flared headless proximal section (123) and a proximal end (152) having a socket (152) for attachment to a tool that can rotate to screw the implant into place;
e. wherein the implant is fully threaded with large pitch cancellous helical threads (142) on the shaft on a portion of the distal section, and smaller pitch cortical helical threads (144) on the shaft on a portion of the proximal section;
f. wherein the implant has a central channel (134) longitudinally spanning the entire length;
g. wherein a set of secondary female threads (170) is in the central channel adjacent to the socket in the proximal end;
h. wherein the implant has one or more fenestrations (160);
i. wherein the implant has a roughened surface; and
j. wherein the implant with the roughened surface is coated with hydroxyapatite (HA) or tri-calcium phosphate (TCP) or both.

15. A fusion or fixation implant for immobilizing the articular surfaces of a joint or segment of bone or fracture comprising:
a. A cylindrical threaded implant fabricated from a titanium or tantalum metal or alloy with a similar modulus of elasticity to bone, wherein the titanium or tantalum metal or alloy is a porous material with pore sizes ranging in 100 to 900 μm and a porosity of 60-65%;
b. wherein the cylinder comprises a shaft (120), wherein the shaft has a diameter between 4 mm to 14 mm and length between 10 mm to 280 mm;
c. wherein the implant has a distal section with a distal end with a rounded tip;
d. wherein the implant has a headless proximal section and a proximal end having a socket for attachment to a tool that can rotate to screw the implant into place;
e. wherein the implant has uniform cortical helical threads on the entire length of the shaft;
f. wherein the implant has a channel through the center with openings at the distal end and proximal end for accepting a guidewire;
g. wherein the implant has one or more fenestrations;
h. wherein the implant has a roughened surface; and
i. wherein the implant with the roughened surface is coated with hydroxyapatite (HA) or tri-calcium phosphate (TCP) or both.

16. The implant of claim 10, wherein a feature with male threads is screwed into the internal female threads (170), wherein the feature is selected from a pedicle screw, an extractor, an inserter, or a cap for the proximal end.

17. The implant of claim 14, wherein a feature with male threads is screwed into the internal female threads (170), wherein the feature is selected from a pedicle screw, an extractor, an inserter, or a cap for the proximal end.

* * * * *